United States Patent [19]

Ohlendorf et al.

[11] Patent Number: 4,705,860

[45] Date of Patent: Nov. 10, 1987

[54] QUATERNARY AMMONIUM SALTS AND THEIR USE AS DRAG REDUCING AGENTS

[75] Inventors: Dieter Ohlendorf, Liederbach; Heinz Hoffmann, Bayreuth; Werner Interthal, Rüsselsheim; Ulrich Pintschovius, Hattersheim am Main, all of Fed. Rep. of Germany

[73] Assignee: Hoechst Aktiengesellschaft, Frankfurt am Main, Fed. Rep. of Germany

[21] Appl. No.: 838,893

[22] Filed: Mar. 11, 1986

Related U.S. Application Data

[63] Continuation of Ser. No. 508,495, Jun. 27, 1983, abandoned.

[30] Foreign Application Priority Data

Jun. 29, 1982 [DE] Fed. Rep. of Germany ....... 3224148

[51] Int. Cl.$^4$ ................. C07D 213/02; C07C 87/30; C07C 87/68
[52] U.S. Cl. ............................ 546/347; 260/501.15; 260/501.21; 564/284; 564/285; 564/288; 564/289; 564/291
[58] Field of Search ............... 546/347; 564/284, 285, 564/288, 289, 291; 260/501.15, 501.21

[56] References Cited

U.S. PATENT DOCUMENTS

| | | | |
|---|---|---|---|
| 2,605,281 | 7/1952 | Blinoff | 260/501.15 |
| 3,236,881 | 2/1966 | Distler et al. | 260/501.15 |
| 4,016,894 | 4/1977 | Baldwin et al. | 137/13 |
| 4,182,765 | 1/1980 | Yagi et al. | 514/368 |

FOREIGN PATENT DOCUMENTS

| | | | |
|---|---|---|---|
| 2334260 | 1/1974 | Fed. Rep. of Germany | 260/501.15 |
| 1518427 | 2/1968 | France | 564/291 |

OTHER PUBLICATIONS

Chem. Abstr. 56:11109i (1962).
Chem. Abstr. 95:27174b (1981).
Chem. Abstr. 95:175879g (1981).
Chem. Abstr. 58:11376d (1963).
White, *Nature*, 214:585–586 (1967).
Hoffmann et al., *Berichte der Bunsengesellschaft fur Physikalische Chemie*, 85: 255–256 (1981).
Gravsholt, Chem. Abstracts, vol. 91(4), abst. No. 91:27461s, Jul. 23, 1979.

*Primary Examiner*—Alan L. Rotman

[57] ABSTRACT

Quaternary ammonium salts of the formula $$R_1 - K^\oplus A^\ominus$$

in which
$R_1$ denotes $C_{12}$–$C_{26}$-alkyl or $C_{12}$–$C_{26}$-alkenyl,
$K^\oplus$ denotes a group of the formula

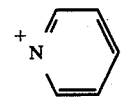

or $-\oplus N(R_2)_3$,
$R_2$ denotes $C_1$–$C_3$-alkyl, preferably methyl, and $A^\ominus$ denotes an anion of one of the following formulae: $R_3SO_3^\ominus$, in which $R_3$ is $C_6$–$C_9$-alkyl or alkenyl and the sum of C atoms in $R_1$ and $R_3$ should be at least 21;

in which

Hal is fluorine, chlorine, bromine or iodine, $R_4$ is $C_1$–$C_5$-alkyl, $C_2$–$C_5$-alkenyl or $C_1$–$C_5$-alkoxy in positions 3, 4, 5 or 6, $R_5$ is hydrogen or hydroxyl in positions 2 or 3, $R_6$ is $COO^-$ or $SO_3^-$ and $R_7$ is hydrogen or methyl, with the exception of the salicylate and m-halogenobenzoate ions when combined with $C_{16}$-alkylpyridinium and $C_{16}$-alkyl- trimethylammonium. These salts are suitable as drag reducing agents in aqueous media with turbulent flow.

3 Claims, 1 Drawing Figure

QUATERNARY AMMONIUM SALTS AND THEIR USE AS DRAG REDUCING AGENTS

This case is a continuation of my copending application, Ser. No. 508,495, filed June 27, 1983, now abandoned.

It is generally known that liquids with turbulent flow encounter frictional resistance on the boundary walls. It is also known that this frictional resistance can be reduced by adding small amounts of certain substances. Substances which have this effect are known as "drag reducing agents" (abbreviated to DRA in the text which follows). A drag reducing agent is therefore understood as a substance which, when added in a small amount to a liquid with turbulent or pulsating flow, enables this liquid to flow more rapidly—under otherwise identical conditions. Drag reducing agents mean that more liquid can be conveyed by a given pump through a given pipeline.

In many cases, just this fact is a technical gain, for example, if a pipeline is charged to full capacity under normal operation and a peak consumption were to be conveyed at certain times. Since more liquid can be conveyed for a given pump output using drag reducing agents, the associated saving in energy is also a technical advantage in many cases. Finally, if it is not the intention to increase throughput, the pressure drop can be reduced or pipes of smaller cross-section can be employed if DRA are used. Both of these measures can improve the economics of operation of the pipeline.

In addition to high-molecular compounds, such as polyethylene oxide and polyacrylamide, solutions of some surfactants are known as drag reducing agents for water or aqueous solutions. However, high-molecular additives have only a limited use in practice as drag reducing agents, since these compounds irreversibly lose their effectiveness as drag reducing agents in areas of high shear stress or tensile stress, such as, for example, in pumps or, to a small degree, in the turbulent interface close to the wall of the pipe, as a result of mechanical degradation. For closed aqueous circulations, such as cooling circulations and district heating networks, in which the same aqueous solution is continuously pumped in circulation through a pipeline system, high-molecular additives are consequently unsuitable since the irreversible mechanical degradation necessitates continuous topping-up with effective high-molecular substance. It is furthermore known that high-molecular additives lose their effectiveness as drag reducing agents above 90° C., and for this reason also they are unsuitable for district heating networks.

As is known, surfactant additives in water do not have the disadvantage of irreversible mechanical degradation (U.S. Pat. No. 3,961,639). Although mechanical degradation can in this case also be observed in areas of very high tensile and shear stress, such as, for example, in pumps, it is fully reversible, as soon as the solution has passed these areas. Thus, the drag-reducing effect of an aqueous solution of Na oleate with addition of KCL+KOH or NACl+NaOH is described by Savins (Rheol. Acta 6, 323 (1967)). Asslanow et al. (Izv. Akad. Nauk. SSSR, Mekh. Zhidk. Gaza 1, 36–43 (1980)) investigated, inter alia, aqueous solutions of Na laurate, myristate, palmitate and stearate at pH 11 as DRA.

Chang et al. (U.S. Pat. No. 3,961,639) have described the drag-reducing effect of aqueous solutions of some non-ionic surfactants with a foreign electrolyte additive at temperatures in the area of the turbidity point.

The essential disadvantages of the surfactant solutions mentioned are their relatively high use concentrations of at least 0.25% by weight, the formation of insoluble soaps with $Ca^{2+}$ and other cations, the formation of two phases which, on prolonged standing, separate and can lead to blockages, the necessity of adding corrosion-promoting foreign electrolytes, and a very narrow temperature range of a few degrees centigrade within which the DRA effect occurs. Aqueous solutions of some cationic surfactants, such as, for example, cetylpyridinium bromide (Inzh. Fizh. Zh. 38, No. 6, 1031–1037 (1980)) or cetyltrimethylammonium bromide (Nature 214, 585–586 (1967)) in each case as a 1:1 molar mixture with α-naphthol, do not have these disadvantages. As well as the poor water-solubility of the α-naphthol, the fact that such mixtures lose their effectiveness as DRA by chemical degradation within a few days should be mentioned as a decisive disadvantage here (U.S. Pat. No. 3,961,639, Conference Proceedings: International Conference on Drag Reduction, 4.-6.9.1974 Rolla Missouri, USA). A further disadvantage of all the surfactant solutions hitherto known is that they lose their effectiveness as DRA above 90° C., and that they are therefore completely unsuitable for district heating networks.

Surprisingly, it has now been found that, in contrast to all the surfactants hitherto known as DRA, the compounds listed below are effective, in the pure form, as drag reducing agents in aqueous solution even in extremely small concentrations, and without any additives at all. It has furthermore been found that, even at temperatures above 90° C. and even under continuous stress, some of these compounds remain effective as DRA for a period of weeks and show no drop in effectiveness.

The invention relates to new quaternary ammonium salts of the formula $$R_1-K^\oplus A^\ominus$$

in which
$R_1$ denotes $C_{12}-C_{26}$-alkyl or $C_{12}-C_{26}$-alkenyl,
$K^\oplus$ denotes a group of the formula or $-\oplus N(R_2)_3$,
$R_2$ denotes $C_1-C_3$-alkyl, preferably methyl, and $A^\ominus$ denotes an anion of one of the following formulae: $R_3SO_3^\ominus$, in which $R_3$ is $C_6-C_9$-alkyl or alkenyl and the sum of the C atoms in $R_1$ and $R_3$ should be at least 21;

-continued in which

Hal is fluorine, chlorine, bromine or iodine, $R_4$ is $C_1$-$C_5$-alkyl, $C_2$-$C_5$-alkenyl or $C_1$-$C_5$-alkoxy in positions 3, 4, 5 or 6, $R_5$ is hydrogen or hydroxyl in positions 2 or 3, $R_6$ is $COO^\ominus$ or $SO_3^\ominus$ and $R_7$ is hydrogen or methyl, with the exception of the salicylate or the m-halogenobenzoate ion when combined with $C_{16}$-alkylpyridinium or $C_{16}$-alkyltrimethylammonium.

The salts of the following cations and anions are particularly preferred.

1.

(a) with the anion $C_6H_{13}SO_3^\ominus$ for $20 \leq n \leq 26$
(b) with the anion $C_7H_{15}SO_3^\ominus$ for $14 \leq n \leq 22$
(c) with the anion $C_8H_{17}SO_3^\ominus$ for $14 \leq n \leq 20$

2.

for $12 \leq n \leq 24$, with the following benzoic acid anions:
(a) 2-phenol-sulfonate, salicylate or m-halogenobenzoate, with the exception of n=16 for the last two anions,
(b)

in which $R_1$ is methyl, ethyl, propyl or $C_nH_{2n+1}O$, with $1 \leq n \leq 4$, preferably in positions 3, 4 or 5 relative to the carboxyl group (c)

in which R is methyl, ethyl, propyl or $C_nH_{2n+1}O$, with $1 \leq n \leq 4$, preferably in positions 4 or 5 relative to the carboxyl group or (d)

in which Hal is F, Cl, Br or I.

3.

for $12 \leq n \leq 24$ with the anions 2-hydroxy-1-naphthoate, 3-(or 4)-hydroxy-2-naphthoate or the corresponding derivatives of naphtholsulfonic acids.

These new quaternary ammonium salts can be prepared as follows.

The alkyl-trimethylammonium halides or pyridinium chlorides, bromides or iodides are first dissolved in anhydrous solvents, such as, for example, methanol, and a slight excess of freshly precipitated silver hydroxide, which has been washed with methanol in the final stage, is added. Thus, as far as possible no water should be introduced into the system, since otherwise difficulties are encountered with the crystallization. On brief warming of the mixture to about 50°, formation of the alkyl-trimethylammonium or pyridinium hydroxide, which remains dissolved in the methanol, takes place.

In this reaction, the brown color of the silver hydroxide largely disappears and the resulting precipitate assumes the color of the silver halide. The silver halide precipitate is then filtered off with suction at about 15°. The alkyltrimethylammonium or pyridinium hydroxide in the methanolic filtrate can be neutralized by addition of the stoichiometric amount of a carboxylic acid, sulfonic acid or inorganic acid. The desired alkyltrimethylammonium salt or pyridinium salt is isolated by evaporating off the methanol.

It is even simpler first to prepare the silver salts of the carboxylic acid in question, these being frequently less water-soluble. Silver hydroxide or silver carbonate can be used as the starting material, and this is neutralized with the desired carboxylic acid. However, it is also possible to dissolve the alkali metal carboxylates in water and to add silver nitrate solution, and the silver carboxylate then precipitates. The silver carboxylate is filtered off with suction, washed and dried. The stoichiometrically required amount of this carboxylate can then be added to a solution of the alkyltrimethylammonium or pyridinium halide in an anhydrous solvent, such as methanol, and the mixture can be warmed briefly to 50° to 60° C.

In this case also, the silver halide is then filtered off with suction at 15° C. and the desired alkyltrimethylammonium or pyridinium carboxylate is isolated by evaporating the filtrate. Preparation in a purer form can be effected by recrystallization from virtually anhydrous solvents (ethyl acetate, acetone, acetonitrile or dichloroethane).

Another possibility which may be mentioned is the preparation of the alkyltrimethylammonium or pyridinium hydroxide solution by treatment of alkyltrimethylammonium or pyridinium halides (or other salts)

with a strongly basic anion exchanger, which also has to be carried out in an anhydrous solvent, such as, for example, methanol. This is again followed by neutralization with the desired carboxylic acid.

The salts mentioned are suitable for reducing the frictional resistance of aqueous media. They are added in concentrations of 0.006 to 2% by weight, preferably 0.04 to 0.4% by weight, but a different lower critical concentration limit for adequate effectiveness as DRA exists for each salt. The effect as DRA also depends on the temperature. Depending on the salt employed, an adequate effect as DRA is found in the temperature range from 0° C. to 90° C., and, for some surfactants also listed below, reduction in friction is even found for the first time above 90° C. The lower temperature limit for use as DRA is, for all surfactants, the solubility temperature. However, if the surfactant is in solution, it is possible for the temperature to fall below the solubility temperature by 5°–20° C. for some hours to weeks.

The n-alkyltrimethylammonium salicylates have been found to have optimum effectiveness as DRA in the following ranges: n-dodecyltrimethylammonium salicylate in the range from 0.14 to 1% by weight from 0° to 30° C.; n-tetradecyltrimethylammonium salicylate in the range from 0.04 to 1% by weight from 5° to 45° C.; n-octadecyltrimethylammonium salicylate in the range from 0.8 to 1% by weight from 40° to 75° C.; and n-docosyltrimethylammonium salicylate in the range from 0.02 to 1% by weight for temperatures from 70° C., in particular above 90° C. In general, the temperature range in which the effect as DRA is sufficient is shifted by about 15° C. towards higher temperatures with each additional $C_2H_4$ group. If the pyridinium compounds are used, the preferred temperature range is about 8°–12° lower in comparison with trimethylammonium salts of the same chain length.

However, the preferred temperature and concentration range is determined not only by the chain length of the n-alkyltrimethylammonium or n-alkylpyridinium compound but also by the type of counter ion.

Thus, for example, the compounds hexadecyltrimethylammonium 3-(or 4)-methylsalicylate or hexadecyltrimethylammonium 4-ethoxysalicylate exhibit an adequate effect as DRA in aqueous solution at 40° C. at from only 0.006% by weight to 1% by weight, and in the concentration range from 0.05 to 1% by weight above 65° C., whilst hexadecyltrimethylammonium salicylate is effective as a DRA from 0.015% by weight at 30° C. and only at concentrations greater than 0.8% by weight above 70° C.

Quite generally, the n-alkyltrimethylammonium and n-alkylpyridinium compounds with the counter ions in which R is $C_1$–$C_5$-alkyl or $C_1$–$C_5$-alkoxy, show a shift in the lower concentration limit for effectiveness as DRA towards smaller values as the chain length of R increases, and at the same time the temperature range is extended to higher values in comparison with the corresponding unsubstituted salicylate compounds. A further increase in the temperature range in which a DRA effect exists is achieved by using surfactants with anions For example, the compounds hexadecyltrimethylammonium 3-(or 4)-hydroxy-2-naphthoate are effective as DRA at 50° C. in the concentration range from 0.005% by weight to 1% by weight, and above 80° C. in the concentration range from 0.025% by weight to 1% by weight. The same applies to the corresponding pyridinium compounds, except that the temperature ranges are on average shifted downwards by about 5°–15° C. Analogously to the salicylate compounds, a change in the chain length of the n-alkyltrimethylammonium and n-alkylpyridinium cation in the hydroxynaphthoates also effects a shift of the temperature range for DRA effect. For example, in each case 1,000 ppm solutions of the compounds n-$C_nH_{2n+1}$trimethylammonium 3-hydroxy-2-naphthoate are effective as DRA from temperatures of 65°–85° C., and also above 105° C. if n is 18, and above 115° C. is n is 20 and furthermore above 125° C. if n is 22. Quite generally, the effective temperature range for the n-alkyltrimethylammonium or n-alkypyridinium 3-hydroxy-2-naphthoates is extended by 30° to 40° C. to higher temperatures in comparison with the particular n-alkyltrimethylammonium or n-alkylpyridinium salicylates.

Similar relationships between the structures of the surfactant salts and the effective temperature and concentration ranges apply to the particular corresponding arylsulfonates. However, the solubility temperatures are frequently higher than in the case of the corresponding arylcarboxylic acids. Thus, for example, n-hexadecyltrimethylammonium 2-phenolsulfonate does not dissolve in water from temperatures as low as 30° C., as does the corresponding salicylate, but dissolves only at temperatures above 50° C. The 2-phenolsulfonate is therefore effective as a drag reducing agent in the temperature range from 50° C. to 70° C. at concentrations from 0.05 to 2% by weight, whilst the corresponding salicylate is already effective from 30° C.

The temperature range and concentration range within which the n-alkyltrimethylammonium n-alkyl-1-sulfonates and n-alkylpyridinium n-alkyl-1-sulfonates are effective as DRA are likewise determined by the chain lengths of the alkyl groups both in the anion and in the cation.

For example, the compound tetradecyltrimethylammonium heptane-1-sulfonate is effective as a DRA in the concentration range from 0.02 to 2% by weight, preferably 0.07 to 0.5% by weight, in the temperature range from 0° C. to 38° C. In contrast, the compound hexadecyltrimethylammonium heptane-1-sulfonate is effective as a DRA in the concentration range from 0.02 to 2% by weight, preferably 0.07 to 0.5% by weight, in the temperature range from 10° C. to 50° C.

A further increase in the chain length of the n-alkyltrimethylammonium or n-alkylpyridinium cation causes a further shift in the effective temperature range to higher temperatures. For example, the compound n-docosyltrimethylammonium n-heptane-1-sulfonate is still effective as a DRA in the concentration range from 0.1 to 1% by weight, even at temperatures above 75° C.

In contrast to the n-heptane-1-sulfonates, the particular corresponding n-octane-1-sulfonates are effective as DRA in a temperature range about 10° to 30° C. higher. For example, the compound n-tetradecyltrimethylammonium n-octane-1-sulfonate is also effective as a DRA above 45° C., and the compound n-octadecyltrimethylammonium n-octane-1-sulfonate is still effective as a DRA in the concentration range from 0.2 to 1% by weight, even above 85° C. In general, lengthening of the n-alkyl chain both in the anions and in the cations causes a shift in the effective temperature range towards higher temperatures.

A clear solution frequently cannot be obtained up to 100° C. with the above surfactants with the anions R—SO$_3\ominus$, in particular with the n-octane-1-sulfonates and 1-nonane-1-sulfonates; this does not impair the effect as DRA.

Of all the surfactants mentioned, those which are particularly suitable as DRA above 90° C. are the salts $C_nH_{2n+1}K^\oplus A^\ominus$, in which $K^\oplus$ represents the quaternary nitrogen group or —N$^+$(R)$_3$, in which R is —CH$_3$ or —C$_2$H$_5$, and A$^-$ includes the following anions:
1. for n≧22: salicylate or 3-halogeno-benzoate, in which halogen is F, Cl, Br or I.
2. for n≧20: 5- or 6-methylsalicylate, methoxysalicylate or n-octane-1-sulfonate.
3. for n≧18: 3- or 4-methyl-2- or -3-hydroxybenzoate, 3- or 4-ethoxy-2- or -3-hydroxybenzoate, n-nonane-1-sulfonate or 2-hydroxy-1-naphthoate.
4. for n≧16: 3- or 4-alkyl-2- or -3-hydroxybenzoate, with C$_2$-C$_4$-alkyl, 3- or 4-alkoxy-2- or -3-hydroxybenzoate with C$_3$-C$_5$-alkyl, or 3- or 4-hydroxy-2-naphthoate.

Compounds which are particularly effective as DRA for temperatures above 100° C. are the salts of group 4 for n≧18; according to Example 23, the compound |C$_{22/20}$H$_{41/45}$N(CH$_3$)$_3$|.3-hydroxy-2-naphthoate, in a concentration of 814 ppm to 1,000 ppm, is still very effective as a DRA at 120° C. to 130° C.

It has furthermore been found that the effectiveness as a DRA either remains unaffected, as, for example, in the case of the sulfonates, or is substantially improved, as, for example, in the case of the hydroxybenzoates and the compounds derived therefrom, by increasing the pH value of the aqueous solution to pH values above 8, preferably to pH 9 to 10.5, by addition of NaOH or other bases, or by addition of Na$_2$CO$_3$ or other salts which increase the pH value. A reduction in the pH value by means of HCl or other strong acids to pH values below 4.5 also has the same influence on the DRA-effect of the surfactants.

The addition of other foreign electrolytes leads to either no influence, such as, for example, in the case of the sulfonates, or an improvement, such as, for example, in the case of the hydroxybenzoates and the compounds derived therefrom, in the effect as a DRA.

Examples of such foreign electrolytes are weak acids, such as acetic acid or formic acid, and salts formed from the following ions: alkali metal, alkaline earth metal, transition metal, ammonium or aluminum cations; halides, ClO$_3\ominus$, ClO$_4\ominus$, BrO$_3\ominus$, JO$_3^{2\ominus}$, S$_2$O$_3^{2\ominus}$, SO$_4^{2\ominus}$, S$_2$O$_8^{2\ominus}$, NO$_2\ominus$, B$_4$O$_7^{2\ominus}$, NO$_3\ominus$, PO$_4^{3\ominus}$, CO$_3^{2\ominus}$, CH$_3$COO$\ominus$, CH$_3$COO$\ominus$, C$_2$O$_4^{2\ominus}$, CN$\ominus$, CrO$_4^{2\ominus}$ or Cr$_2$O$_7^{2\ominus}$. The maximum amount of these foreign electrolytes which can be added to the aqueous surfactant solution is limited by the concentration at which a salting out effect for the surfactant occurs, together with a decrease or the complete disappearance of the effectiveness as a DRA.

The action of the foreign electrolytes also depends on the valency of the ions, and in particular the action is shifted towards lower concentrations in accordance with the following scheme: 1-1-valent electrolyte<2-1-valent electrolyte<1-2-valent electrolyte<2-2-valent electrolyte<3-2-valent electrolyte<2-3-valent electrolyte. The improvement in the effectiveness as a drag reducing agent in the case of the hydroxybenzoates and the compounds derived therefrom is particularly marked when a salt which at the same time increases the pH value to pH≧9.9 is added. Thus, for example, the addition of Na$_2$CO$_3$ in the concentration range from 0.1 C–10 C, where C is the molar concentration of the surfactant employed, has a particularly advantageous effect.

Instead of adding salts, it is also possible to use the halogen salt of the cationic surfactant R$_1$K$^+$Hal$^-$, such as, for example, in which Hal is Cl, Br or I, in a molar ratio of 1:1 with an alkali metal salt of the anion NaA, such as, for example, Na n-alkyl-1-sulfonate, Na hydroxy-benzoate or Na hydroxy-naphthoate, as the drag reducing agent. The effect is then equal to the effect which is achieved with the pure surfactant salts with addition of alkali metal halides. Mixtures which deviate from the molar ratio of 1:1, such as, for example, to 1:2, also still have an effect as DRA. The maximum effectiveness as drag reducing agents also depends on the time which has elapsed since the preparation of the aqueous surfactant solutions. Although the surfactant solutions already show an effect as drag reducing agents immediately after the solutions have been prepared, this effect can still change significantly during one week. The time required to achieve an optimum effect can easily be determined for the individual case by simple experiments. In most cases, the optimum effect is achieved after one week. No further change or improvement in effect then occurs.

Some surfactants, such as, for example, hexadecylpyridinium salicylate, are known (H. Hoffmann et al., Ber. Bunsenges. Phys. Chem. 85 (1981) 255) to build up large, non-spherical, usually rod-shaped micelles from the individual surfactant ions and counter ions above a quite specific concentration, the CMC$_{II}$, characteristic for each surfactant.

Surprisingly, it has now been found that surfactants in aqueous solution are always effective as drag reducing agents if they form non-spherical, preferably rod-shaped, micelles for concentrations greater than the CMC$_{II}$. Non-spherical, preferably rod-shaped micelles are present if, when the surfactant solution is examined with the aid of the method of electrical double refraction with a pulsed, rectangular electrical field (E. Fréderitq and C. Houssier, Electric Dichroism and Electric Birefringence, Clarendon Press, Oxford 1973 and H. Hoffmann et al., Ber. Bunsenges. Phys. Chem. 85 (1981) 255), a measurement signal is found, from the drop in which a relaxation time of $\tau \geq 0.05$ μs can be determined. The lower concentration limit above which a surfactant in aqueous solution is effective as a drag reducing agent is therefore always given by the $CMC_{II}$, preferably by 1.5 times the concentration value of the $CMC_{II}$. The $CMC_{II}$ can be determined, for example, by measuring the electrical conductivity of the surfactant solution as a function of the surfactant concentration, as described by H. Hoffmann et al. (Ber. Bunsenges. Phys. Chem. 85 (1981) 255). It has been found that the $CMC_{II}$ value depends on the temperature and shifts to higher surfactant concentrations as the temperature increases.

Determination of the $CMC_{II}$ at the use temperature with the aid of the electrical conductivity is a suitable preliminary experiment to determine the minimum surfactant concentration required to achieve an adequate action as a DRA in a particular temperature range.

The effectiveness of the above surfactants as DRA has in most cases been investigated in the conventional manner by measuring the pressure drop $\Delta P$ over the length L when the particular aqueous solution of the surfactants flows through a pipe of diameter d at various flow rates u. The dimensionless parameters of coefficient of friction $\lambda$ and the Reynolds number Re can be calculated from these values as follows:

$$\lambda = \frac{2d}{\rho u^2} \cdot \frac{\Delta P}{L}$$

$$Re = \frac{u d}{\gamma}$$

in which $\rho$ denotes the density and $\gamma$ denotes the kinematic viscosity. The appropriate values of the pure solvent, i.e. water, are usually used for $\rho$ and $\gamma$. The values $\lambda$ and Re thus obtained for the surfactant solutions investigated were compared in the conventional double-logarithmic plot of $\lambda$ against Re with the corresponding values for pure water, represented by $$1/\sqrt{\lambda} = 2 \log Re \sqrt{\lambda} - 0,8$$

An effect as a DRA or a reduction in friction exits if: $\lambda_{H2O} - \lambda_{SB} > 0$, and the reduction in friction in percent is calculated from the equation:

$$\alpha = \% \text{ reduction in friction} = \frac{2H_2O - 2SB}{H_2O} \times 100$$

Figure 1:
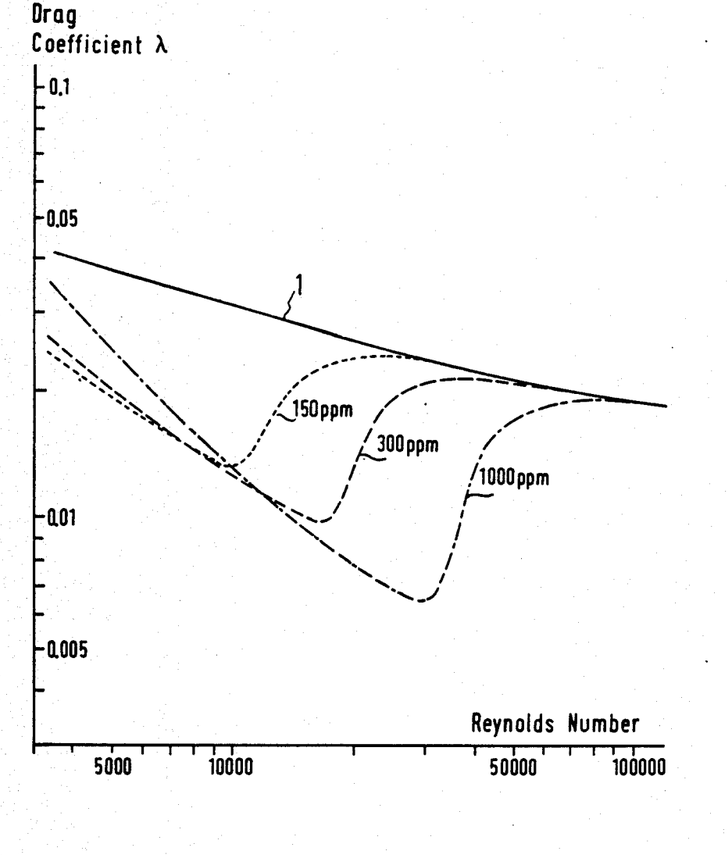

As can be seen from FIG. 1, the above surfactant solutions are effective as DRA in that the percentage reduction in friction increases as the Reynolds number increases, but then decreases again very rapidly after a certain Reynolds number, $Re_{max}$, has been exceeded, with maximum percentage reduction in friction. The degree of effectiveness of a surfactant solution as a DRA is characterised in the following text by the parameter $Re_{max}$; accordingly, a surfactant solution with $Re_{max} = 20,000$ is more effective as a DRA than a surfactant solution with $Re_{max} = 10,000$. The associated $\alpha$-value is characterised by $\alpha_{max}$. The investigations on the surfactant solutions usually gave reproducible results only when the aqueous solutions of the surfactant salts had been stored at the measurement temperatures for in each case about 1 week before the measurements. Although the solutions also display an effect as drag reducing agents immediately after being prepared, this effect can still change significantly in the course of one week.

The surfactants treated in this way were subjected to a large number of tests. Thus, long-term experiments lasting many days showed, as can be seen from Example 22, that no drop in the drag reducing effect of the surfactants mentioned occurred as a result of mechanical or chemical degradation. It was furthermore found that the effectiveness of the above surfactants as DRA increases as the concentration increases; however, the viscosity of the solutions also increases, so that the percentage reduction in friction becomes worse at lower Reynolds numbers, as can be seen from FIG. 1.

The investigations carried out show that the above surfactant salts are suitable as drag reducing agents in all cases where water is pumped through pipelines, but especially where water is continuously pumped in circulation through a pipeline system, such as, for example, in cooling circulations, since long-term stability of the DRA, as shown by the above surfactant salts, is absolutely necessary here. In addition, some of the surfactants mentioned are particularly suitable for district heating networks, since these surfactants even retain their effect as drag reducing agents for weeks under stress above 90° C. (see Example 22).

The surfactant salts can be metered into the water flowing through the pipelines either in the form of a concentrated surfactant solution (1–10% by weight) or by adding the pure crystalline surfactant salts. Metering into the pipeline system shortly before a pump is the most advantageous point, because of the good mixing effect.

EXAMPLE 1

42.0 g of silver nitrate are dissolved in 175 g of water. With stirring, this silver nitrate solution is stirred into a sodium hydroxide solution prepared from 11.5 g of sodium hydroxide (99% pure) and 35 g of water. The silver hydroxide precipitate formed is filtered off with suction and washed four times with water and then four times with methanol. The (methanol-moist) material on the filter is added to a solution of 72.9 g of cetyl-trimethylammonium bromide (commercially available) in 600 ml of methanol. The mixture is warmed briefly (2 minutes) to 60° and is cooled to about 10° and the silver bromide formed is filtered off with suction. The filtrate is a water-white, clear solution of cetyl-trimethylammonium hydroxide in methanol. It is divided into three equal parts and the first third is neutralized by addition of 10.29 g of m-cresotic acid [4-methyl-2-hydroxy-benzoic acid]. After the methanol solution has been evaporated on a rotary evaporator, 29.0 g of a colorless powder are obtained, which can be purified by repeated recrystallization from (400) ml of ethyl acetate: colorless platelets.

This compound can be titrated with perchloric acid in glacial acetic acid.

EXAMPLE 1a AND 1b

The cetyl-trimethylammonium hydroxide can also be neutralized with 3-methyl-2-hydroxy-benzoic acid (1a) and cetyl=hexadecyl. with 5-methyl-2-hydroxy-benzoic acid (1b) in the same way. The products are also obtained in the form of colorless platelets by recrystallization from ethyl acetate.

EXAMPLE 2

A second third of the cetyl-trimethylammonium hydroxide solution can be neutralized by addition of 12.71 g of 3-hydroxy-2-naphthoic acid (EW by titration 190.6). After concentration of this solution to dryness in a rotary evaporator, 30.5 g of a slightly brownish powder are obtained.

Recrystallization from 300 ml of acetone gives the 3-hydroxy-2-naphthoate as light yellow crystals (titration with perchloric acid in glacial acetic acid).

EXAMPLE 3

The last third of the cetyl-trimethylammonium hydroxide solution is neutralized with 12.39 g of 4-ethoxy-2-hydroxy-benzoic acid (the equivalent weight of which has been determined as 185.8 by titration with 0.1N sodium hydroxide solution) by scattering in as a powder. The resulting yellow solution in methanol is concentrated to dryness. 31.1 g of a slightly brownish residue are obtained, which can be purified by recrystallization from 300 ml of ethyl acetate several times. Cetyl-trimethylammonium 4-ethoxysalicylate is obtained in (slightly reddish) crystals (titration with perchloric acid in glacial acetic acid gives the expected equivalent weight).

EW = equivalent weight.

EXAMPLE 4

24.5 g of Na heptane-1-sulfonate monohydrate are dissolved in 35 g of water. This solution is stirred into a solution of 18.1 g of silver nitrate in 25 g of water. The silver salt which deposits is filtered off with suction and rinsed twice with a little methanol. After drying, 26.2 g (85.3% of theory) of silver heptane-1-sulfonate are obtained as a colorless crystalline powder.

37.2 g of silver heptane-1-sulfonate are added to a solution of 37.74 g of tetradecyl-trimethylammonium chloride in 250 ml of methanol. After warming for a short time, the silver chloride is filtered off with suction; the water-clear filtrate is concentrated in a rotary evaporator: 55.5 g of crude product.

Crystallization from 350 ml of dichloroethane gives tetradecyltrimethylammonium heptane-1-sulfonate in the form of large colorless platelets.

EXAMPLE 5

Sparingly soluble silver salicylate is prepared from 64.2 g of sodium salicylate and 67.96 g of silver nitrate in water. 110 g of docosyl-trimethyl-ammonium bromide are introduced into 300 ml of methanol. 59.6 g of silver salicylate (finely powdered) are added.

The reaction mixture is heated briefly to 60° C., filtered with suction at 15° and evaporated (122 g of residue).

Recrystallization from 500 ml of isopropanol gives docosyltrimethylammonium salicylate in the form of colorless platelets (which can be titrated with perchloric acid in glacial acetic acid).

EXAMPLE 6

A concentration series of 300, 500, 750, 1,000 and 1,500 ppm by weight of tetradecyltrimethylammonium heptane-1-sulfonate (abbreviated to $C_{14}TA$ heptane-1-sulfonate) demineralized water was made up by weighing out the corresponding amounts by weight of 0.3; 0.5; 0.75; 1.0 and 1.5 g of $C_{14}TA$ heptane-1-sulfonate per 1,000 g of demineralized water. During the dissolving operation, the solutions were heated briefly to about 90° C., with stirring, and, after cooling to room temperature (23° C.), the solutions were stored at this temperature for 1 week, without being stirred.

The reduction in friction was then investigated in a turbulence rheometer (Polymer Letters 9,851 (1971)), by forcing 1.5 liters of liquid through the measurement tube with the aid of a piston, analogously to a syringe. The movement of the piston is accelerated during the measurement, so that the entire flow curve, as shown in FIG. 1, is recorded in one measurement. The diameter of the measurement tube is 3 mm, and the measurement length for ΔP is 300 mm and the running-in length is 1,200 mm.

The same concentration series of $C_{14}TA$ heptane-1-sulfonate was measured in this apparatus at 23° C. and 35° C., after the solution had likewise first been stored at 35° C. for 1 week.

The results of all the measurements at 23° C. and 35° C. are summarized in Tables 1 and 2 by giving the $Re_{max}$ and $\alpha_{max}$.

EXAMPLE 7

Various amounts of $Na_2CO_3$ were made up into aqueous solutions together with $C_{14}TA$ heptane-1-sulfonate, as described in Example 6, the concentrations of $C_{14}TA$ heptane-1-sulfonate in each case being 750 ppm (1.72 moles/liter) and those of $Na_2CO_3$ (in moles/liter) being chosen as follows: $1\times10^{-4}$; $2\times10^{-4}$; $1\times10^{-3}$; $1.72\times10^{-3}$; 0.01 and 0.1.

The results of the investigation into reduction in friction at 23° C. in a turbulence rheometer are summarized in Table 3. As can be seen from Table 3, up to $1.72\times10^{-3}$ moles/liter of $Na_2CO_3$ has no effect, and above 10 times the molar excess, the effect of $C_{14}TA$ heptane 1-sulfonate as a DRA is impaired.

EXAMPLE 8

Aqueous solutions of differing concentration of $C_{14}TA$ heptane-1-sulfonate were prepared by weighing the salts $C_{14}TA$ Cl and Na heptane-1-sulfonate in a molar mixing ratio of 1:1, at total concentrations of 500, 1,000, 1,500 and 2,000 ppm, as described in Example 6. The results of the investigation into the reduction in friction in a turbulence rheometer are summarized in Table 4. As can be seen from Table 4, the additional equimolar amount of NaCl does not influence the reduction in friction effected by $C_{14}TA$ heptane-1-sulfonate.

EXAMPLE 9

Aqueous solutions of n-alkyltrimethylammonium n-alkyl-1-sulfonate with different alkyl radicals were prepared, as described in Example 8, by weighing out the n-alkyltrimethylammonium chloride and Na alkyl-1-sulfonate salts in a molar mixing ratio of 1:1. The results of the investigation into the reduction in friction in a turbulence rheometer for the various surfactants are summarized in Table 5. The equimolar amounts of NaCl which the solutions additionally contain are not shown.

EXAMPLE 10

As described in Example 6, a concentration series of 500, 750, 1,000 and 1,500 ppm by weight of tetradecyltrimethylammonium salicylate (abbreviated to $C_{14}TA$ Sal) was made up, pretreated and measured in a turbulence rheometer at 23°, 40° and 45° C. The results of the investigation into the reduction in friction are summarized in Table 6.

EXAMPLE 11

As described in Example 7, various amounts of $Na_2CO_3$ were made into aqueous solutions together with $C_{14}TA$ Sal, and the solutions were investigated for reduction in friction in a turbulence rheometer at 23° C. The concentration of $C_{14}TA$ Sal was in each case 750 ppm ($=1.91\times10^{-3}$ moles/liter) and the concentrations of $Na_2CO_3$ (in moles/liter) were $1\times10^{-4}$; $2\times10^{-4}$; $1\times10^{-3}$; $1.78\times10^{-3}$; 0.01 and 0.1. The results are summarised in Table 7.

EXAMPLE 12

As described in Example 6, aqueous solutions of n-alkyltrimethylammonium salicylates (($C_nH_{2n+1}N(CH_3)_3$ salicylate, abbreviated to $C_nTA$ Sal) with different alkyl radicals were prepared, stored at different temperatures and investigated for the reduction in friction in a turbulence rheometer. In addition, an 800 ppm solution of $C_{18}TA$ Sal was adjusted to pH 11 with NaOH, an equimolar amount of NaCl ($2\times10^{-3}$ moles/liter) was added to a further 1,000 ppm solution of $C_{18}TA$ Sal and both solutions were likewise investigated in a turbulence rheometer. From Table 8, in which the results are summarized, it can be seen that both increasing the pH value and adding the foreign electrolytes cause a significant improvement in the effect as a DRA.

EXAMPLE 13

As described in Example 6, aqueous solutions of n-hexadecyltrimethylammonium 3-methyl-salicylate (abbreviated to $C_{16}TA$ 3-methyl-Sal) were made up, pretreated and investigated for the reduction in friction in a turbulence rheometer at various temperatures. The results are summarized in Table 9. The flow curves at 50° C. for 150, 300 and 1,000 ppm solutions of $C_{16}TA$ 3-methyl-Sal are shown in FIG. 1. (1) shows the curve measured for pure water.

EXAMPLE 14

As described in Example 6, aqueous solutions of n-hexadecyltrimethylammonium 4-methyl-salicylate (abbreviated to $C_{16}TA$ 4-methyl-Sal) were prepared, pretreated and investigated for the reduction in friction in a turbulence rheometer at various temperatures. As can be seen from the summary of the results in Table 10, a reduction in friction at 24° C. was found with as little as 60 ppm.

EXAMPLE 15

As described in Example 6, aqueous solutions of n-hexadecyltrimethylammonium 4-ethoxy-salicylate (abbreviated to $C_{16}TA$ 4-ethoxy-Sal) were prepared and were investigated for the reduction in friction in a turbulence rheometer. The results are summarized in Table 11.

EXAMPLE 16

As described in Example 6, aqueous solutions of n-hexadecyltrimethylammonium 3-hydroxy-4-methyl-benzoate (abbreviated to $C_{16}TA$ 3-hydroxy-4-methyl-benzoate) were prepared and investigated for the reduction in friction in a turbulence rheometer at 23° C. The results are summarized in Table 12.

EXAMPLE 17

As described in Example 6, aqueous solutions of n-hexadecyltrimethylammonium 2-hydroxy-1-naphthoate ($C_{16}TA$ 2-hydroxy-1-naphthoate) were prepared and investigated for the reduction in friction in a turbulence rheometer at 68° C. The results are summarized in Table 13.

EXAMPLE 18

As described in Example 6, aqueous solutions of n-hexadecyltrimethylammonium 3-hydroxy-2-naphthoate ($C_{16}TA$ 3-hydroxy-2-naphthoate) were made up, pretreated and investigated for the reduction in friction in a turbulence rheometer at 68°, 80° and 93° C. As can be seen from Table 14, in which the measurement results are summarized, this surfactant is effective as a DRA even above 90° C.

EXAMPLE 19

Various amounts of $Na_2CO_3$ were made up into aqueous solutions together with $C_{16}TA$ 3-hydroxy-2-naphthoate as described in Example 7. The concentration of $C_{16}TA$ 3-hydroxy-2-naphthoate was in each case 200 ppm ($4.25\times10^{-4}$ moles/liter) and the concentrations of $Na_2CO_3$ (in moles/liter) were $1\times10^{-4}$; $2\times10^{-4}$; $4.24\times10^{-4}$; 0.005; 0.05 and 0.5.

Two further 200 ppm solutions of $C_{16}TA$ 3-hydroxy-2-naphthoate were adjusted to pH values of 10.6 and 11.4 with NaOH and were then likewise pretreated as described in Example 1. All the solutions were investigated for reduction in friction in a turbulence rheometer at 65° C. The results are summarized in Table 15.

EXAMPLE 20

As described in Example 8, aqueous solutions of n-alkyltrimethylammonium 3-hydroxy-2-naphthoates ($C_nTA$ 3-hydroxy-2-naphthoates) with different alkyl radicals were prepared by weighing out the n-alkyltrimethylammonium chloride salt, 3-hydroxy-2-naphthoic acid and NaOH in a molar ratio of 1:1:1, and were investigated for the reduction in friction in a turbulence rheometer. The results are summarized in Table 16. The equimolar amounts of NaCl which the solutions additionally contain have not been shown separately.

EXAMPLE 21

As described in Examples 20 and 8, aqueous solutions of various surfactants, such as $C_{14}TA$ naphthalene-1-hydroxy-2-sulfonate, $C_{14}TA$ 3-chloro-benzoate, $C_{16}TA$ 4-methyl-benzoate, $C_{16}TA$ 3-nitro-benzoate and $C_{16}TA$ naphthalene-1-hydroxy-2-sulfonate, are prepared by weighing out the particular n-alkyltrimethylammonium chloride salts, the aromatic acids and NaOH in a molar ratio of 1:1:1, and are investigated for the reduction in friction in a turbulence rheometer. The results are summarized in Table 17. The equimolar amounts of NaCl which the solutions contain are not shown.

EXAMPLE 22

A flow apparatus consisting of a 400 liter stock vessel, a centrifugal pump (type: CPK 50-250 from KSB, speed of rotation of the rotor: 1,450 revolutions per minute), an inductive flow meter and a pipeline 20 m in length with an internal diameter of 29.75 mm was used to investigate the reduction in friction in a long-term test at 84° to 90° C. The pressure drop ΔP was determined over a measurement length of 1 m. An immersion heater which heated the liquid in the stock vessel electrically was used for thermostatic control. During the long-term experiment, the liquid was pumped off continuously from the bottom of the stock vessel and was recycled to the stock vessel via the pipeline. The delivery of the pump for demineralized water at 84° C. was 14.7 m³/hour, corresponding to a flow rate u of 5.88 m/second, and the pressure drop ΔP was 7,000 Pa.

The stability with respect to time of the drag reducing agent n-hexadecyltrimethylammonium 3-hydroxy-2-naphthoate in aqueous solution at a concentration of 640 ppm was measured in this apparatus at 84° to 90° C. For this, 198 g of hexadecyltrimethylammonium bromide, 102 g of 3-hydroxy-2-naphthoic acid and 21.7 g of NaOH, i.e. all 3 salts in a molar mixing ratio of 1:1:1, were added to 400 liters of demineralized water in the running apparatus. The pH value was adjusted to 10 by weighing out an additional equimolar amount of $Na_2CO_3$ (57.6 g). The full effect as a drag reducing agent was established, as a result of continuous pumping of the solution in circulation, only 10 minutes after addition of the salts, and manifested itself in that the delivery of the pump rose to 21 m³/hour, corresponding to a flow rate of 8.5 m/second, and the pressure drop over the measurement length additionally fell to ΔP×4,200 Pa.

The % reduction in friction α was calculated by the equations already given (pages 18-19), the coefficient of friction for pure demineralized water, $\lambda_{H2O}$, however, being calculated theoretically for the Re number resulting from the increased delivery of the pump after addition of the DRA.

The results of the long-term experiment, i.e. the time in days, the temperature T, the Reynolds number Re and the % reduction in friction α, are summarized in Table 18.

As the results show, no drop in the DRA effect is to be found over a period of 14 days at a temperature of 84°-90° C., even using a centrifugal pump which pumps the contents of the stock vessel in circulation 53.5 times per hour or 1,284 times per day.

EXAMPLE 23

For measurements above 100° C., aqueous solutions of n-alkyltrimethylammonium 3-hydroxy-2-naphthoates ($C_n$TA 3-hydroxy-2-naphthoates) were prepared as described in Example 8 by weighing out the n-alkyltrimethylammonium chloride salts, 3-hydroxy-2-naphthoic acid and NaOH in a molar ratio of 1:1:1. A solution of $C_{20/22}$TA salicylate was also made up from the salts $C_{20/22}$TA Cl and Na salicylates. In contrast to Example 6, however, these solutions were stored at 95° C. for only about 20 hours, and were then thermostatically controlled at the particular measurement temperature for in each case half an hour before each measurement in a turbulence rheometer. As can be seen from the summary of the results of investigation into the reduction in friction in the turbulence rheometer, shown in Table 19, a reduction in friction was found in the temperature range from 110° to 130° C. The effect as a DRA was retained even after repeated heating and measurement of the solutions at the particular temperatures.

EXAMPLE 24

As described in Example 6, a concentration series of 500, 750 and 1,500 ppm by weight of hexadecyltrimethylammonium 2-phenol-sulfonate ($C_{16}$TA 2-phenolsulfonate) was prepared, pretreated and measured in a turbulence rheometer at 50° C. A solution with a concentration of 3,000 ppm by weight of $C_{16}$TA 2-phenolsulfonate in water was measured at 64° C. The results are summarized in Table 20.

EXAMPLE 25

As described in Example 7, various amounts of NaCl were made up into aqueous solutions together with $C_{16}$TA 2-phenolsulfonate and the solutions were investigated for the reduction in friction in a turbulence rheometer at 55° C. The concentration of $C_{16}$TA 2-phenolsulfonate was in each case 750 ppm ($=2.27\times10^{-3}$ moles/liter) and the concentrations of NaCl (in moles/liter) were $5\times10^{-5}$; $1\times10^{-4}$; $5\times10^{-4}$; $2.27\times10^{-3}$; $6\times10^{-3}$ and $1\times10^{-2}$. The results are summarized in Table 21.

TABLE 1

$C_{14}$TA heptane-1-sulfonate

| T [°C.] | Concentration [ppm] | $Re_{max}$ | $\alpha_{max}$ (% reduction in friction) |
| --- | --- | --- | --- |
| 23 | 300 | 6100 ± 600 | 60 ± 3 |
| 23 | 500 | 9800 ± 1000 | 65 ± 3 |
| 23 | 750 | 15100 ± 1500 | 68 ± 3 |
| 23 | 1000 | 19200 ± 1900 | 68 ± 3 |
| 23 | 1500 | 22700 ± 2300 | 71 ± 4 |

TABLE 2

$C_{14}$TA heptane-1-sulfonate

| T [°C.] | Concentration [ppm] | $Re_{max}$ | $\alpha_{max}$ (% reduction in friction) |
| --- | --- | --- | --- |
| 35 | 300 | — | no effect |
| 35 | 500 | — | no effect |
| 35 | 750 | 12100 ± 1200 | 21 ± 1 |
| 35 | 1000 | 17000 ± 1700 | 42 ± 2 |
| 35 | 1500 | 19900 ± 2000 | 46 ± 2 |

TABLE 3

Measurement temperature: 23° C., $C_{14}$TA heptane-1-sulfonate Concentration: 750 ppm

| $Na_2CO_3$ concentration [mol/l] | $Re_{max}$ | $\alpha_{max}$ |
| --- | --- | --- |
| $1\times10^{-4}$ | 14100 ± 1400 | 67 ± 3 |
| $2\times10^{-4}$ | 15400 ± 1500 | 68 ± 3 |
| $1\times10^{-3}$ | 14700 ± 1500 | 68 ± 3 |
| $1,72\times10^{-3}$ | 15800 ± 1600 | 68 ± 3 |
| 0,01 | 12200 ± 200 | 67 ± 3 |
| 0,1 | 6500 to 19000 | 20 to 30 |

TABLE 4

Measurement temperature: 23° C., 1:1 molar mixtures of $C_{14}$TACl and Na heptane-1-sulfonate.

| Concentration of the mixture [ppm] | $Re_{max}$ | $\alpha_{max}$ |
| --- | --- | --- |
| 500 | 9900 ± 1400 | 67 ± 3 |
| 1000 | 16600 ± 1700 | 68 ± 3 |
| 1500 | 20800 ± 2100 | 68 ± 3 |
| 2000 | 23500 ± 2400 | 70 ± 4 |

TABLE 5

| Surfactants | | Concentration [ppm] | Temperature [°C.] | $Re_{max}$ | $\alpha_{max}$ |
|---|---|---|---|---|---|
| $C_{16}TA^\oplus$ | $C_6H_{13}SO_3^\ominus$ | 2000 | 22 | 7900 ± 800 | 56 ± 3 |
| $C_{18}TA^\oplus$ | $C_6H_{13}SO_3^\ominus$ | 2000 | 22 | 4500 ± 500 | 24 ± 1 |
| $C_{22/22}TA^\oplus$ | $C_6H_{13}SO_3^\ominus$ | 2000 | 45 | 33600 ± 3400 | 70 ± 4 |
| $C_{16}TA^\oplus$ | $C_7H_{15}SO_3^\ominus$ | 1000 | 45 | 13600 ± 1400 | 56 ± 3 |
| $C_{18}TA^\oplus$ | $C_7H_{15}SO_3^\ominus$ | 1000 | 45 | 6700 ± 700 | 47 ± 2 |
| $C_{20/22}TA^\oplus$ | $C_7H_{15}SO_3^\ominus$ | 1000 | 80 | 4000 ± 400 | 35 ± 2 |
| $C_{14}TA^\oplus$ | $C_8H_{17}SO_3^\ominus$ | 2000 | 45 | 18200 ± 1800 | 70 ± 4 |
| $C_{16}TA^\oplus$ | $C_8H_{17}SO_3^\ominus$ | 2000 | 45 | 41800 ± 4200 | 75 ± 4 |
| $C_{18}TA^\oplus$ | $C_8H_{17}SO_3^\ominus$ | 2000 | 80 | 46000 ± 4600 | 73 ± 4 |
| $C_{20/22}TA^\oplus$ | $C_8H_{15}SO_3^\ominus$ | 2000 | 90 | 17800 ± 1800 | 68 ± 3 |

$C_nTA+$ in each case represents $[C_nH_{2n+1}N(CH_3)_3]^\oplus$

TABLE 6
$C_{14}TA$ Sal

| T [°C.] | Concentration [ppm] | $Re_{max}$ | $\alpha_{max}$ |
|---|---|---|---|
| 23 | 500 | 12600 ± 1300 | 65 ± 3 |
| 23 | 750 | 15500 ± 1600 | 68 ± 3 |
| 23 | 1000 | 21000 ± 2100 | 69 ± 3 |
| 23 | 1500 | 27100 ± 2700 | 72 ± 3 |
| 40 | 500 | 7900 ± 800 | 13 ± 0,5 |
| 40 | 750 | 9000 ± 900 | 56 ± 3 |
| 40 | 1000 | 14100 ± 1400 | 68 ± 3 |
| 40 | 1500 | 21900 ± 2200 | 74 ± 4 |
| 45 | 1000 | 14000 ± 1400 | 20 ± 1 |
| 45 | 1500 | 18500 ± 1900 | 49 ± 2 |

TABLE 7
Temperature: 23° C., $C_{14}TA$ Sal concentration: 750 ppm

| $Na_2CO_3$ concentration [mol/l] | pH | $Re_{max}$ | $\alpha_{max}$ |
|---|---|---|---|
| $1 \times 10^{-4}$ | 8,6 | 15000 | 65 ± 3 |
| $2 \times 10^{-4}$ | 8,4 | 16100 | 68 ± 3 |
| $1 \times 10^{-3}$ | 9,8 | 16700 | 68 ± 3 |
| $1,78 \times 10^{-3}$ | 10,5 | 18400 | 69 ± 3 |
| 0,01 | 10,5 | 17800 | 70 ± 4 |
| 0,1 | 11 | 14000 | 67 ± 3 |

TABLE 8

| Surfactant | Concentration [ppm] | T [°C.] | $Re_{max}$ | $\alpha_{max}$ |
|---|---|---|---|---|
| $C_{12}TA$-Sal | 1500 | 23 | 21200 ± 2100 | 40 ± 2 |
| $C_{18}TA$-Sal | 800 | 60 | 4500 ± 500 | 31 ± 2 |
| $C_{18}TA$-Sal(*) | 800 | 60 | 17300 ± 1700 | 71 ± 4 |
| $C_{18}TA$-Sal | 1000 | 60 | 5400 ± 500 | 35 ± 2 |
| $C_{18}TA$-Sal(**) | 1000 | 60 | 18400 ± 1800 | 71 ± 4 |
| $C_{22}TA$-Sal | 500 | 90 | 18500 ± 1900 | 65 ± 3 |
| $C_{22}TA$-Sal | 1000 | 90 | 22000 ± 2200 | 60 ± 3 |

(*)solution was adjusted to pH 11 with NaOH
(**)solution contained $2 \times 10^{-3}$ moles/liter of NaCl

TABLE 9
$C_{16}TA$ 3-methyl-Sal

| T [°C.] | Concentration [ppm] | $Re_{max}$ | $\alpha_{max}$ |
|---|---|---|---|
| 23 | 100 | 6700 ± 700 | 59 ± 3 |
| 23 | 150 | 8700 ± 900 | 61 ± 3 |
| 23 | 300 | 8900 ± 900 | 63 ± 3 |
| 23 | 1500 | 12100 ± 1200 | 63 ± 3 |
| 50 | 150 | 9800 ± 1000 | 62 ± 3 |
| 50 | 300 | 16700 ± 1700 | 66 ± 3 |
| 50 | 1000 | 33800 ± 3400 | 74 ± 4 |
| 68 | 300 | 17900 ± 1800 | 65 ± 3 |
| 68 | 1000 | 34100 ± 3400 | 71 ± 4 |

TABLE 10
$C_{16}TA$ 4-methyl-Sal

| T [°C.] | Concentration [ppm] | $Re_{max}$ | $\alpha_{max}$ |
|---|---|---|---|
| 24 | 60 | 4400 ± 400 | 57 ± 3 |
| 24 | 80 | 6300 ± 600 | 56 ± 3 |
| 24 | 90 | 6900 ± 700 | 57 ± 3 |
| 22 | 100 | 6300 ± 600 | 58 ± 3 |
| 22 | 150 | 9000 ± 900 | 64 ± 3 |
| 22 | 300 | 10800 ± 1100 | 63 ± 3 |
| 22 | 1000 | 10900 ± 1100 | 64 ± 3 |
| 50 | 150 | 10100 ± 1000 | 61 ± 3 |
| 50 | 300 | 17100 ± 1700 | 67 ± 3 |
| 50 | 1000 | 34400 ± 3400 | 74 ± 4 |
| 68 | 300 | 15500 ± 1500 | 65 ± 3 |
| 68 | 1000 | 34200 ± 3400 | 72 ± 4 |

TABLE 11
$C_{16}TA$ 4-ethoxy-Sal

| T [°C.] | Concentration [ppm] | $Re_{max}$ | $\alpha_{max}$ |
|---|---|---|---|
| 24 | 100 | 6000 ± 600 | 59 ± 3 |
| 24 | 150 | 9000 ± 900 | 58 ± 3 |
| 24 | 300 | 13200 ± 1300 | 68 ± 3 |
| 24 | 500 | 15700 ± 1600 | 66 ± 3 |
| 45 | 2000 | 45900 ± 4600 | 77 ± 4 |

TABLE 12
$C_{16}TA$ 3-hydroxy-4-methyl-benzoate

| T [°C.] | Concentration [ppm] | $Re_{max}$ | $\alpha_{max}$ |
|---|---|---|---|
| 23 | 100 | 5800 ± 600 | 62 ± 3 |
| 23 | 150 | 6700 ± 700 | 60 ± 3 |
| 23 | 300 | 9400 ± 900 | 65 ± 3 |
| 23 | 1000 | 11700 ± 1200 | 65 ± 3 |
| 23 | 2000 | 17700 ± 1800 | 69 ± 4 |

TABLE 13
$C_{16}TA$ 2-hydroxy-1-naphthoate

| T [°C.] | Concentration [ppm] | $Re_{max}$ | $\alpha_{max}$ |
|---|---|---|---|
| 68 | 200 | 16000 ± 1600 | 67 ± 3 |
| 68 | 300 | 22100 ± 2200 | 70 ± 4 |
| 68 | 400 | 32800 ± 3300 | 72 ± 4 |
| 68 | 750 | 43400 ± 4300 | 72 ± 4 |
| 68 | 1000 | 60400 ± 6000 | 78 ± 4 |

TABLE 14
$C_{16}TA$ 3-hydroxy-2-naphthoate

| T [°C.] | Concentration [ppm] | $Re_{max}$ | $\alpha_{max}$ |
|---|---|---|---|
| 68 | 100 | 11000 ± 1200 | 59 ± 3 |
| 68 | 200 | 18800 ± 1900 | 68 ± 3 |
| 68 | 300 | 29700 ± 3000 | 72 ± 4 |
| 68 | 400 | 35300 ± 3500 | 75 ± 4 |
| 68 | 500 | 41700 ± 4200 | 75 ± 4 |
| 68 | 750 | 49800 ± 5000 | 77 ± 4 |
| 68 | 1000 | 59200 ± 6000 | 75 ± 4 |
| 80 | 200 | 14700 ± 1500 | 66 ± 3 |
| 80 | 300 | 21400 ± 2100 | 68 ± 3 |
| 80 | 400 | 29800 ± 3000 | 70 ± 4 |

TABLE 14-continued

| | $C_{16}TA$ 3-hydroxy-2-naphthoate | | |
|---|---|---|---|
| T [°C.] | Concentration [ppm] | $Re_{max}$ | $\alpha_{max}$ |
| 80 | 500 | 35300 ± 3500 | 72 ± 4 |
| 80 | 750 | 48300 ± 4800 | 75 ± 4 |
| 80 | 1000 | 57000 ± 5700 | 75 ± 4 |
| 93 | 500 | 28000 ± 2800 | 77 ± 4 |
| 93 | 750 | 40000 ± 4000 | 79 ± 4 |
| 93 | 1000 | 52000 ± 5200 | 74 ± 4 |

TABLE 15

Temperature: 65° C., $C_{16}TA$ 3-hydroxy-2-naphthoate concentration: 200 ppm

| $Na_2CO_3$ concentration [mol/l] | pH | $Re_{max}$ | $\alpha_{max}$ |
|---|---|---|---|
| 1 × 10$^{-4}$ | 7,6 | 18300 ± 1800 | 65 ± 3 |
| 2 × 10$^{-4}$ | 10,1 | 19200 ± 1900 | 67 ± 3 |
| 4,24 × 10$^{-4}$ | 10,3 | 20400 ± 2000 | 68 ± 3 |
| 5 × 10$^{-3}$ | 10,8 | 19700 ± 2000 | 70 ± 4 |
| 0,05(*) | 11,4 | 18100 ± 1800 | 68 ± 3 |
| 0,5(*) | 11,7 | 15100 ± 1500 | 63 ± 3 |
| NaOH | 10,6 | 20100 ± 2000 | 63 ± 3 |
| addition | 11,4 | 17300 ± 1700 | 65 ± 3 |

(*)Solutions contained small amounts of precipitate.

TABLE 16

| | $C_nTA$ 3-hydroxy-2-naphthoate + NaCl | | |
|---|---|---|---|
| $C_nTA$ | T [°C.] | Concentration [ppm] | $Re_{max}$ | $\alpha_{max}$ |
| $C_{12}TA$ | 45 | 2000 | 23200 ± 2300 | 47 ± 2 |
| $C_{14}TA$ | 55 | 2000 | 52800 ± 5300 | 78 ± 2 |
| $C_{18}TA$ | 90 | 300 | 21400 ± 2100 | 68 ± 3 |

$C_nTA$ in each case represents $[C_nH_{2n+1}N(CH_3)_3]^+$

TABLE 17

| Surfactant | Concentration [ppm] | T [°C.] | $Re_{max}$ | $\alpha_{max}$ |
|---|---|---|---|---|
| $C_{14}TA$ 3-chloro-benzoate | 2000 | 22 | 22700 ± 2300 | 71 ± 4 |
| $C_{14}TA$ naphthalene-1-hydroxy-2-sulfonate | 2000 | 22 | 23100 ± 2300 | 36 ± 2 |
| $C_{16}TA$ 4-methyl-benzoate | 5000 | 22 | 25800 ± 2600 | 65 ± 3 |
| $C_{16}TA$ 3-nitro-benzoate | 5000 | 22 | 8600 ± 900 | 50 ± 3 |
| $C_{16}TA$ naphthalene-1-hydroxy-2-sulfonate | 2000 | 22 | 20300 ± 2000 | 69 ± 3 |

$C_nTA$ in each case represents $[C_nH_{2n+1}N(CH_3)_3]^+$

TABLE 18

Long-term experiment with $C_{16}TA$ 3-hydroxy-2-naphthoate (640 ppm)

| Time [days] | Temperature [°C.] | $Re_{max}$ | $\alpha_{max}$ |
|---|---|---|---|
| 0,01 | 84 | 727000 | 72 ± 4 |
| 4 | 85 | 740000 | 73 ± 4 |
| 5 | 84 | 732000 | 73 ± 4 |
| 6 | 90 | 773000 | 71 ± 4 |
| 7 | 90 | 773000 | 71 ± 4 |
| 10 | 90 | 769000 | 70 ± 4 |
| 12 | 90 | 765000 | 70 ± 4 |
| 14 | 90 | 729000 | 68 ± 3 |

TABLE 19

| Surfactant | T [°C.] | Concentration [ppm] | $Re_{max}$ | $\alpha_{max}$ |
|---|---|---|---|---|
| $C_{20/22}TA$ salicylate | 110 | 3000 | 5400 ± 500 | 44 ± 2 |
| $C_{18}TA$ 3-hydroxy-2-naphthoate | 110 | 1000 | 60600 ± 6100 | 70 ± 4 |
| $C_{18}TA$ 3-hydroxy-2-naphthoate | 115 | 1000 | 42600 ± 4300 | 62 ± 3 |
| $C_{20/22}TA$ 3-hydroxy-2-naphthoate | 120 | 814 | 50200 ± 5000 | 60 ± 3 |
| $C_{20/22}TA$ 3-hydroxy-2-naphthoate | 132 | 1000 | 34000 ± 3400 | 45 ± 2 |

TABLE 19-continued

| Surfactant | T [°C.] | Concentration [ppm] | $Re_{max}$ | $\alpha_{max}$ |
|---|---|---|---|---|
| 2-naphthoate | | | | |

$C_nTA$ in each case represents $[C_nH_{2n+1}N(CH_3)_3]^+$

TABLE 20

| | $C_{16}TA$ 2-phenolsulfonate | | |
|---|---|---|---|
| T [°C.] | Concentration [ppm] | $Re_{max}$ | $\alpha_{max}$ |
| 50 | 500 | 6700 ± 700 | 58 ± 3 |
| 50 | 750 | 8500 ± 900 | 60 ± 3 |
| 50 | 1500 | 16400 ± 1600 | 65 ± 3 |
| 65 | 3000 | 36600 ± 3700 | 71 ± 4 |

TABLE 21

Measurement temperature: 55° C., $C_{16}TA$ 2-phenolsulfonate concentration: 750 ppm

| NaCl concentration [mol/l] | $Re_{max}$ | $\alpha_{max}$ |
|---|---|---|
| 5 10$^{-5}$ | 7400 ± 700 | 65 ± 3 |
| 1 10$^{-4}$ | 10100 ± 1000 | 64 ± 3 |
| 5 10$^{-4}$ | 12200 ± 1200 | 67 ± 3 |
| 2 27 10$^{-3}$ | 12100 ± 1200 | 71 ± 4 |
| 6 10$^{-3}$ | 11600 ± 1200 | 44 ± 2 |
| 0,01 | 20200 ± 2000 | 70 ± 4 |
| 0,05 | no reduction in friction | |

We claim:

1. A quaternary ammonium salt of the formula $$R_1-K^{\oplus}A^{\ominus}$$

in which $R_1$ denotes $C_{12}-C_{26}$-alkyl or $C_{12}-C_{26}$-alkenyl, $K^{\oplus}$ denotes a group of the formula $$-\overset{\oplus}{N}\diagup\!\!\!\diagdown$$

or $-^{\oplus}N(R_2)_3$, $R_2$ denotes $C_1-C_3$-alkyl, and $A^{\ominus}$ denotes an anion of one of the following formulae:

[structures: salicylate (COO⁻, OH on benzene); R₄/R₅-substituted benzoate with COO⁻; R₇-substituted naphthalene with OH and COO⁻]

in which $R_4$ is $C_1$–$C_5$-alkyl, $C_2$–$C_5$-alkenyl or $C_1$–$C_5$-alkoxy in positions 3, 4, 5 or 6, $R_5$ is hydrogen or hydroxyl in positions 2 or 3, and $R_7$ is hydrogen or methyl, with the exception of the salicylate ion when combined with $C_{16}$-alkyl-pyridinium or $C_{16}$-alkyltrimethylammonium.

2. A quaternary ammonium salt as claimed in claim 1, wherein $R_2$ is methyl.

3. A quaternary ammonium salt as claimed in claim 1, wherein $A^-$ denotes an anion of the formula in which R is $C_1$–$C_5$-alkyl or $C_1$–$C_5$-alkoxy in positions 4, 5 or 6.

* * * * *